United States Patent [19]

Regnat et al.

[11] Patent Number: 5,789,623
[45] Date of Patent: Aug. 4, 1998

[54] PROCESS FOR THE PREPARATION OF HYDROXYBIARYLPHOSPHINES AND NOVEL COMPOUNDS OF THIS GROUP OF SUBSTANCES

[75] Inventors: Dieter Regnat, Eppstein; Hans-Jerg Kleiner, Kronberg, both of Germany

[73] Assignee: Hoechst Aktiengesellschaft, Germany

[21] Appl. No.: 661,629

[22] Filed: Jun. 11, 1996

[30] Foreign Application Priority Data

Jun. 12, 1995 [DE] Germany ............... 195 21 340.8

[51] Int. Cl.$^6$ .................................................. C07F 9/52
[52] U.S. Cl. ................................. 568/16; 568/17
[58] Field of Search .......................... 568/16, 17

[56] References Cited

U.S. PATENT DOCUMENTS

| | | | |
|---|---|---|---|
| 5,523,437 | 6/1996 | Hayashi | 556/21 |
| 5,530,150 | 6/1996 | Takaya | 556/18 |

FOREIGN PATENT DOCUMENTS

| | | |
|---|---|---|
| 0614903 | 9/1994 | European Pat. Off. |
| A 614903 | 9/1994 | European Pat. Off. |
| A 647647 | 4/1995 | European Pat. Off. |

OTHER PUBLICATIONS

Bardella, F., et al, *Tetrahedron Letters* 31:6231–6234 (1990).
Uozumi, Y., et al, *J. Org. Chem.* 58:1945–1948 (1993).
CA:123:198277, Abst of EP614870, "Process and chiral rhodium hydroformylation catalysts for preparing optically active aldehydes", Takaya, Sep. 1994.
CA:121:9662, Abst of "Synthesis of new chiral phosphineophosphite etc", Tetrahedron Lett 35(13) 2023–6, Higashizima, 1994.
CA:119:180104, Abst of "Highly enantioselective hydroformylationof olefins catalyzed by new phosphine phosphite-rhodium I complexes", J Am Chem Soc. 115(15) 7033–4, Sakai, 1993.
E. A. Chernyshev et al, "Journal of General Chemistry of the USSR", *Organophosphorus Heterocyclic Compounds, III. Synthesis and Reactions of 6–Chloro–6H–Dibenz|c,e||1,2| Oxaphosphorine*, pp. 88–90, Jul. 12, 1972.

*Primary Examiner*—Gary Geist
*Assistant Examiner*—Jean Vollano
*Attorney, Agent, or Firm*—Connolly & Hutz

[57] ABSTRACT

The present invention relates to a hydroxybiarylphosphines of the formula

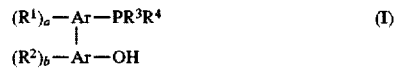

in which Ar-Ar is biphenyl, 1-phenyinaphthyl or 1,1'-binaphthyl, $R^1$ and $R^2$ are identical or different and are F or alkoxy having in each case 1 to 8 carbon atoms or are substituted or unsubstituted aryl, a and b are identical or different and are an integer from 0 to 4, in which $R^3$ and $R^4$ are identical or different and are alkyl having 1 to 8 carbon atoms, cycloalkyl having 4 to 10 carbon atoms, alkaryl having 7 to 9 carbon atoms, $Ar^3$—$(R^5)_n$, in which $A^3$ is an aryl radical having 6 to 10 carbon atoms, $R^5$ is $CF_3$, dialkylamino having a total of 2 to 8 carbon atoms or —$CH_2N(alkyl)_2$ having 1 to 3 carbon atoms per alkyl and n is an integer from 0 to 5, or —$R^3$—$R^4$— forms a chain of 3 to 5 members to which one or two aromatic rings or ring systems having 6 to 10 carbon atoms are optionally fused together with the P atom, forms a ring having 4 to 6 members, with the proviso that $Ar^3$—$(R^5)_n$ is not phenyl or a phenyl substituted by halogen, alkyl or alkoxy each having 1 to 8 carbon atoms, if Ar-Ar is bipohenyl or 1,1'-binaphthyl and a=b=0 and $R^3$ and $R^4$ are identical in each case.

11 Claims, No Drawings

PROCESS FOR THE PREPARATION OF HYDROXYBIARYLPHOSPHINES AND NOVEL COMPOUNDS OF THIS GROUP OF SUBSTANCES

BACKGROUND OF THE INVENTION

The present invention relates to a process which is improved with respect to the prior art for the preparation of hydroxybiarylphosphines and novel compounds of this group of substances.

Hydroxybiarylphosphines are important intermediates, for example in the synthesis of phosphinophosphite ligands of the formula (A)

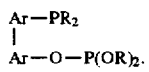

The abovementioned posphinophosphite ligands are used in enantioselective hydroformylation (EP 0 614 901, EP 0 614 902, EP 0 614 903, EP 0 614 870). By means of enantio-selective hydroformylation, by reacting a suitable olefin with carbon monoxide and hydrogen, optically active aldehydes, for example, can be prepared.

The preparation of the hydroxybiarylphosphines required as intermediates for the preparation of the phosphinophosphite ligands is described in more detail in EP 0 614 903 and in Tetrahedron Letters, 31, 6321 (1990) and J. Org. Chem. 58, 1945 (1993).

It starts from dihydroxybiaryl compounds and proceeds via not less than 4 stages, described in more detail by the reaction equations below. Some of these reaction stages are costly and are associated, furthermore, with high expenditure for the necessary purification steps. The reaction proceeds via the following 4 stages:

1st stage

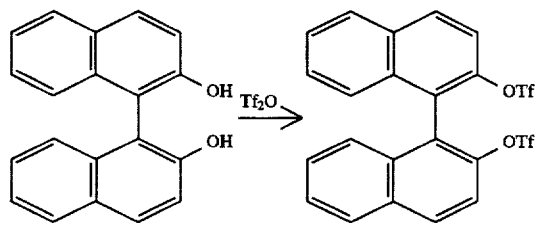

Tf$_2$O: Trifluoromethylsulfonic anhydride

OTf: trifluoromethylsulfonic acid radical (F$_3$CSO$_3$)$^-$

2nd stage

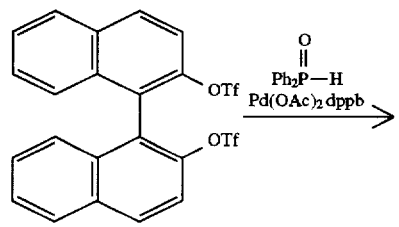

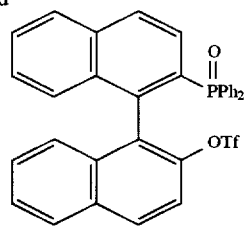

Ph$_2$P—H: diphenylphosphine oxide

Pd(OAc)$_2$: palladium acetate
dppb: 1,4-bis(diphenyphosphino)butane
Ph: phenyl

3rd stage

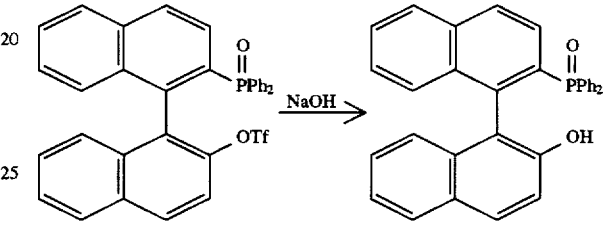

4th stage

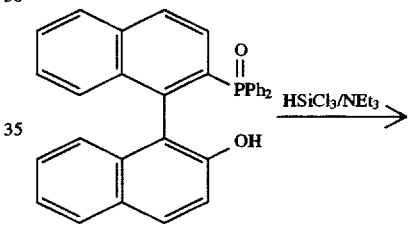

HSiCl$_3$: Trichlorosilane
NEt$_3$: Triethylamine

A further disadvantage of this process is that a disubstituted phosphine oxide, that is diphenylphosphine oxide, must be employed in the second stage. However, only a restricted number of suitable disubstituted phosphine oxides are available. This considerably restricts the possibilities of this synthesis.

A further critical disadvantage is the fact that diphenylphosphine oxide reacts at random with one of the two TfO radicals. This reaction is therefore not suitable for specifically substituting one of the two TfO radicals by the diphenylphosphine oxide radical. A mixture of both substitution products always forms. This is a disadvantage, in particular, when unsymmetrical dihydroxybiaryl compounds are used, since mixtures form which cannot be separated into the individual components, or can only be separated with a disproportionately high expenditure.

This process is therefore chiefly suitable only for the reaction of symmetrical dihydroxybiaryl compounds in which the two hydroxyl groups are identical in the sense of being indistinguishable. In this case, it does not actually matter which of the two hydroxyl groups or TfO radicals are exchanged for the diphenylphosphine oxide, since an exchange of the one hydroxyl group or of the one TfO radical always leads to the same end product as exchange of the other hydroxyl group or of the other TfO radical.

There is therefore vigorous interest in providing a process for the preparation of hydroxybiarylphosphines which does not have the above described disadvantages, can be implemented industrially without great expense starting from comparatively readily accessible starting materials, does not start from dihydroxybiaryl compounds and is therefore also not restricted to the reaction of symmetrical dihydroxybiaryl compounds.

SUMMARY OF THE INVENTION

An object of the invention is achieved by a process for the preparation of hydroxybiarylphosphines of the formula

(I)

in which $R^1$, $R^2$, a, b, Ar-Ar, $R^3$ and $R^4$ have the meaning below. The process comprises reacting an oxaphosphorine of the formula

(II)

in which Ar-Ar is biphenyl, 1-phenylnaphthyl or 1,1'-binaphthyl, $R^1$ and $R^2$ are identical or different and are F, Cl, alkyl or alkoxy having in each case 1 to 8 carbon atoms or are substituted or unsubstituted aryl, preferably having from 6–10 carbon atoms and can optionally be substituted preferably with at least one $R^5$ which is defined below, a and b are identical or different and are an integer from 0 to 4, X in each case is Cl or Br and the Ar-P and the Ar-O bond are each arranged in the orthoposition to the Ar-Ar bond, with a compound $R^3$-Me and $R^4$-Me, in which $R^3$ and $R^4$ are identical or different and are alkyl having 1 to 8 carbon atoms, cycloalkyl having 4 to 10 carbon atoms, alkaryl having 7 to 9 carbon atoms, $Ar^3$-$(R^1)_n$, in which $Ar^3$ is an aryl radical having 6 to 10 carbon atoms, $R^5$ is alkyl or alkoxy having in each case 1 to 8 carbon atoms, F, Cl, $CF_3$, dialkylamino having a total of 2 to 8 carbon atoms or —$CH_2N$ (alkyl)$_2$ having 1 to 3 carbon atoms per alkyl and n is an integer from 0 to 5, or with a compound Me-$R^3$-$R^4$-Me, in which —$R^3$-$R^4$— forms a chain of 3 to 5 members to which one or two aromatic rings or ring systems having 6 to 10 carbon atoms are optionally anellated, Me is a monovalent metal or one equivalent of a polyvalent metal, in the presence of a solvent at a temperature of about –40' to about 160° C., then adding water and, optionally a water-insoluble organic solvent and separating the aqueous phase from the organic phase.

The reaction proceeds, as described for example by the equation below, with cleavage of the P ring in the oxaphosphorine (II):

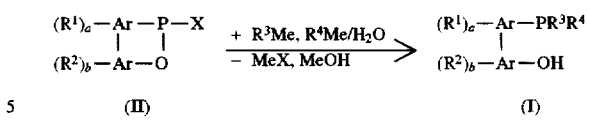

It is to be considered as highly surprising that it is possible using the process of the invention to open the phosphorus-containing ring in the oxaphosphorine of the formula (II) with very high selectivity, not only the Ar-Ar bond, but also at the same time the Ar-P bond remaining unchanged.

This ensures that even when unsymmetrical oxaphosphorines are used, a uniform hydroxybiarylphosphine is always formed and not a mixture containing various hydroxybiarylphosphines and other by-products and breakdown products.

Furthermore, the process of the invention permits the phosphorus atom to be specifically substituted either by two identical radicals or by two different radicals.

The process of the invention, moreover, starts from comparatively readily accessible oxaphosphorines of the formula (II) whose preparation is subject-matter of a German patent application (File number: 195 21 339.4) filed on the same day as the present patent application.

A further advantage of the process of the invention is that it is not necessary to isolate one of the intermediates between the individual working steps in order then to process this further.

In order to illustrate which oxaphosphorines of the formula (II) can be used, the following compounds of the formulae (II), (IIIa), (IV), (IVa) and (V) may be mentioned, but without making in this case any claim as to completeness of the enumeration.

The oxaphosphorines of the formula (III)

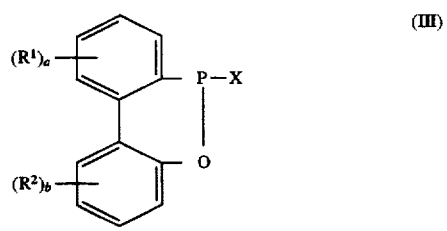

(III)

are derived from 6-chloro-6H-dibenz[c,e][1,2]oxaphosphorine or 6-bromo-6H-dibenz[c,e][1,2]oxaphosphorine. The oxaphosphorine of the formula (IIIa)

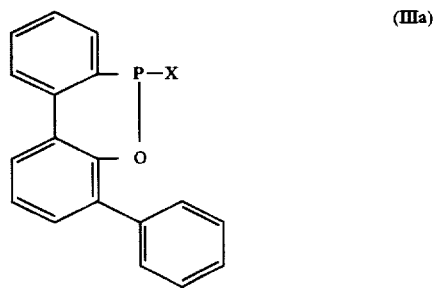

(IIIa)

is 6-chloro-6H-4-phenyldibenz[c,e][1,2]oxaphosphorine or 6-bromo-6H-4-phenyldibenz[c,e][1,2]oxaphosphorine. The oxaphosphorines of the formula (IV) containing a 1-phenylnaphthyl radical as Ar-Ar

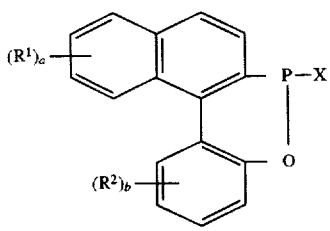

(IV)

are derived from 6-chloro-6H-benzo[e]naphth[2,1-c][1,2]-oxaphosphorine or 6-bromo-6H-benzo[e]naphth[2,1-c][1,2]-oxaphosphorine and the oxaphosphorines of the formula (IVa) similarly containing a 1-phenylnaphthyl radical as Ar-Ar

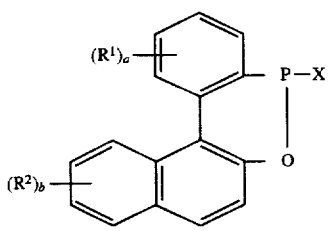

(IVa)

are derived from 5-chloro-5H-benzo[c]naphth[1,2-c][1,2]-oxaphosphorine or 5-bromo-5H-benzo[c]naphth[1,2-c][1,2]-oxaphosphorine.

The oxaphosphorines of the formula (V) containing a binaphthyl radical as Ar-Ar

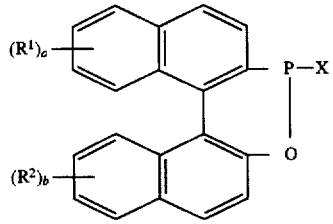

(V)

are derived from 3-chloro-3H-dinaphtho[2,1-c:1',2'-e]-[1,2]oxaphosphorine or 3-bromo-3H-dinaphtho[2,1c:1',2'-e]-[1,2]oxaphosphorine.

It is understood that, in the abovementioned formulae, $R^1$, $R^2$, a and b have the meaning already given.

Compounds of particular interest are oxaphosphorines of the formula (II) in which $R^1$ and $R^2$ have the meaning mentioned above and a is 0 and b is 1 or a is 1 and b is 0. These oxaphosphorines are relatively readily accessible, since they only have one radical $R^1$ and $R^2$, and at the same time they are unsymmetrical. Particular preference is to be given to oxaphosphorines of the formula (II) in which a and b are each 0.

The process of the invention can be carried out with great success by using an oxaphosphorine of the formula (II), in which $R^1$ and $R^2$ are identical or different and are F, Cl, alkyl or alkoxy having in each case 1 to 4 carbon atoms or are substituted or unsubstituted phenyl, a and b are identical or different and are an integer from 0 to 2, in particular a is 0 and b is 1 or a is 1 and b is 0, and by using, in particular, an oxaphosphorine of the formula (II), in which $R^1$ and $R^2$ are identical or different and are F, Cl, alkyl or alkoxy having in each case 1 to 4 carbon atoms, a and b are identical or different and are 0 or 1, in particular a and b are different and are 0 or 1.

According to a process variant, an oxaphosphorine of the formula (II) is used, in which Ar-Ar is 1-phenylnaphthyl and the Ar-P bond is arranged on the phenyl ring of the 1-phenylnaphthyl or on the naphthyl ring of the 1-phenylnaphthyl. These oxaphosphorines can, as already described by the compounds of the formulae (IV) and (IVa), be substituted by $(R^1)_a$ and $(R^1)_b$, oxaphosphorines of this type, in which a is 0 and b is 1 or a is 1 and b is zero or in which a and b are each zero, because of their relatively good availability, achieving particular interest.

As compounds $R^3$-Me and/or $R^4$-Me or Me-$R^3$-$R^4$-Me, in which $R^3$-$R^4$ are joined together and form a chain having 3 to 5 carbon atoms and the chain can be substituted or unsubstituted, in particular one or two aromatic rings or ring systems each having 6 to 10 carbon atoms can be anellated to the chain, use can generally be made of organometallic compounds. Me is, for example, $MgX^1$, where $X^1$ is chlorine, bromine or iodine, in particular chlorine or bromine, or an alkali metal, for example lithium, sodium or potassium, in particular sodium or lithium, preferably lithium.

The reaction is carried out in the presence of a solvent. It is advisable to use as solvent a dipolar aprotic solvent or a nonpolar solvent or a mixture of these solvents.

In this context, it may be noted that organometallic compounds are usually handled in specific solvents. Grignard compounds are frequently used dissolved or suspended in an ether.

The solvents used can be, without making any claim as to the completeness, an ether or an ether mixture, for example dialkyl ether having 2 to 4 carbon atoms per alkyl, tetrahydrofuran, dioxane, toluene, ortho-xylene, meta-xylene, para-xylene, a mixture of isomeric xylenes, mesitylene, ethylbenzene or mixtures of these solvents.

The reaction is presumed to proceed in two stages, one equivalent of the organometallic compound first reacting with the oxaphosphorine. In this case, the X on the P atom in the oxaphosphorine of the formula (II) is probably substituted.

In a subsequent stage, a further equivalent of the organometallic compounds reacts with the previously substituted P atom of the oxaphosphorine, the ring probably being opened by cleavage of the P-O bond.

Utilizing this reaction sequence, the oxaphosphorine of the formula (II) can first be reacted with the compound $R^3$-Me and then with the compound $R^4$-Me or, vice versa, the oxaphosphorine of the formula (II) can first be reacted with the compound $R^4$-Me and then with the compound $R^3$-Me.

By this means, hydroxybiarylphosphines of the formula I are obtained in a simple manner whose P atom, because of the substitution by two different radicals $R^3$ and $R^4$, has in total three different radicals, that is the hydroxybiaryl radical, the radical $R^3$ and the radical $R^4$.

This reaction sequence can of course also be applied to the reaction of the compound Me-$R^3$-$R^4$-Me, the phosphorus atom being incorporated into a ring.

In most cases it is sufficient to carry out the reaction at a temperature of about 40° to about 160° C., in particular about 60° to about 120° C. This relates to the entire reaction sequence, that is both stages.

However, the reaction can also be allowed to proceed in a first stage at about −40° to about 80°, in particular about −20° to about 60°, preferably about −10° to about 50, ° C. and then in a second stage at about 20° to about 160°, in particular about 40° to about 140°, preferably about 60° to about 120° C.

The reaction conditions also depend to a certain extent on the type of organometallic compound used.

Organometallic compounds having a high reactivity, for example alkyl-Grignard compounds or alkali metal alkyls, can be reacted even at very low temperatures, whereas less reactive organometallic compounds, for example aryl-Grignard compounds, necessitate higher reaction temperatures. However, the reaction conditions also depend to a certain extent on the type of the oxaphosphorine used. Oxaphosphorines of the formula (II) having elevated reactivity can be reacted at lower temperatures. These may include oxaphosphorines whose P-containing ring is under stress, for example owing to twisting of the two aryl radicals with respect to each other about the Ar-Ar bond. Oxaphosphorines whose P-containing ring has no stress, or only low stress, or oxaphosphorines whose P atom is sterically hindered owing to bulky substituents and is not freely accessible to an attack by the organometallic compound can, in contrast, make a reaction at elevated temperatures necessary.

Usually, a solution of the oxaphosphorine of the formula (II) is introduced, one of the abovementioned solvents being able to be used. A solution or suspension of the organometallic compound $R^3$-Me, $R^4$-Me or Me-$R^3$-$R^4$-Me is added dropwise with stirring to this solution. The organometallic compound is used in the stoichiometrically required amount or in a stoichiometric excess.

In the first reaction stage, about 1.0 to about 1.5, in particular about 1.0 to about 1.3, mol of the organometallic compounds $R^3$-Me or $R^4$-Me or Me-$R^3$-$R^4$-Me are added per mol of oxaphosphorine of the formula (II), and in the second reaction stage, about 1.0 to about 1.5, in particular about 1.0 to about 1.3, mol of the organometallic compounds $R^3$-Me or $R^4$-me are added per mol of oxaphosphorine of the formula (II).

The reaction proceeds in the absence of water, due to the use of the water-sensitive organometallic compounds. It is advisable to allow the reaction to proceed under a protective gas atmosphere, for example under anhydrous $N_2$ or argon.

The procedure can alternatively be performed the other way round and the solution or suspension of the organometallic compound can be introduced and the oxaphosphorine or the solution of the oxaphosphorine can be added with stirring.

After completion of the reaction, the reaction mixture is cooled, if a high reaction temperature should make this necessary, and water is added. The addition of water is necessary in order to hydrolyse any organometallic compounds still present and to hydrolyse the products formed due to the reaction.

In order to promote or induce the phase separation, a water-insoluble organic solvent can be added to the reaction mixture. Usually, toluene, ortho-xylene, meta-xylene, para-xylene, mixtures of isomeric xylenes, mesitylene, ethylbenzene, esters which are derived from a carboxylic acid, in particular an aliphatic carboxylic acid having 1 to 8, in particular 1 to 4, carbon atoms and an aliphatic alcohol having 1 to 8, in particular 1 to 4, carbon atoms, for example ethyl, propyl or butyl acetate, are suitable for use as water-insoluble organic solvent.

In some cases, it can be useful to adjust the reaction mixture or the aqueous phase contained therein to a pH ≦ about 10. This additionally promotes the phase separation. Usually it is sufficient to set a pH of about 3 to about 9, in particular about 4 to about 8, preferably about 5 to about 7. The phases are then separated, the organic phase, generally containing the product of value, is dried and concentrated, for example by distilling off the solvent under reduced pressure.

The hydroxybiarylphosphines of the formula (I) are usually further purified by crystallization.

The process of the invention may be carried out continuously or discontinuously, particularly simply discontinuously. It may be carried out at superatmospheric pressure, atmospheric pressure or reduced pressure, particularly simply under the reaction pressure which establishes itself.

The present invention further relates to novel hydroxybiarylphosphines of the formula I

in which Ar-Ar is biphenyl, 1-phenylnaphthyl or 1,1'-binaphthyl, in particular 1-phenylnaphthyl. $R^1$ and $R^2$ are identical or different and are F, Cl, alkyl or alkoxy having in each case 1 to 8 carbon atoms or are substituted or unsubstituted aryl, wherein the aryl can preferably have 1 to 10 carbons atoms and can optionally be substituted with at least one $R^5$, a and b are identical or different and are an integer from 0 to 4, and the Ar-P and the Ar-O bond are each arranged in the ortho-position to the Ar-Ar bond, $R^3$ and $R^4$ are identical or different and are alkyl having 1 to 8 carbon atoms, cycloalkyl having 4 to 10 carbon atoms, alkaryl having 7 to 9 carbon atoms, $Ar^3$-$(R^5)_n$, in which $Ar^3$ is an aryl radical having 6 to 10 carbon atoms, $R^5$ is alkyl or alkoxy having in each case 1 to 8 carbon atoms, F, Cl, $CF_3$, dialkylamino having a total of 2 to 8 carbon atoms or —$CH_2N(alkyl)_2$ having 1 to 3 carbon atoms per alkyl and n is an integer from 0 to 5, or —$R^3$-$R^4$— forms a chain of 3 to 5 members to which one or two aromatic rings or ring systems having 6 to 10 carbon atoms are optionally anellated, and, together with the P atom, forms a ring having 4 to 6 members, with the proviso that $Ar^3$-$(R^5)_n$ is not phenyl or a phenyl substituted by halogen, alkyl or alkoxy each having 1 to 8 carbon atoms, if Ar-Ar is biphenyl or 1,1'-binaphthyl and $R^3$ and $R^4$ are identical in each case.

The invention relates in particular to hydroxybiarylphosphines of the formula (I), in which Ar-Ar is biphenyl, 1-phenylnaphthyl or 1,1'-binaphthyl, in particular 1-phenylnaphthyl, $R^1$ and $R^2$ are identical or different and are F, Cl, alkyl or alkoxy having in each case 1 to 4 carbon atoms or substituted or unsubstituted phenyl, a and b are identical or different and are an integer from 0 to 2, in particular 0 or 1.

The invention further relates to hydroxybiarylphosphines of the formula (I), in which Ar-Ar is biphenyl, 1-phenylnaphthyl or 1,1'-binaphthyl, in particular 1-phenylnaphthyl, $R^3$ and $R^4$ are identical or different and are alkyl having 1 to 4 carbon atoms, cycloalkyl having 4 to 6 carbon atoms, benzyl, $Ar^3$-$(R^5)$, where $Ar^3$ is an aryl radical having 6 to 10 carbon atoms, $R^5$ is alkyl or alkoxy having in each case 1 to 4 carbon atoms, F, Cl, $CF_3$, dialkylamino having a total of 2 to 8 carbon atoms or —$CH_2N(alkyl)_2$ having 1 to 3 carbon atoms per alkyl and n is an integer from 0 to 5, with the proviso that $Ar^3$-$(R^5)_n$ is not phenyl or a phenyl substituted by halogen, alkyl or alkoxy having in each case 1 to 8 carbon atoms, if Ar-Ar is biphenyl or 1,1'-binaphthyl and $R^3$ and $R^4$ are identical.

In the event that Ar-Ar is 1-phenylnaphthyl, a feature of the novel hydroxybiarylphosphines is that the radical —$PR^3R^4$ is arranged either on the phenyl ring of the 1-phenylnaphthyl or on the naphthyl ring of the 1-phenylnaphthyl.

Without making any claim as to completeness, the following substances may be mentioned as novel compounds:
2-diphenylphosphino-1-(2-hydroxyphenyl)naphthalene,
2-dicyclohexylphosphino-1-(2-hydroxyphenyl)naphthalene,
2-bis-(4-fluorophenyl)phosphino-1-(2-hydroxyphenyl)-naphthalene,
2-bis-(2-methoxyphenyl)phosphino-1-(2-hydroxyphenyl)-naphthalene, 2-bis-(2-methylphenyl)phosphino-1-(2-hydroxyphenyl)-naphthalene,
2-(4-fluorophenyl-phenyl)phosphino-1-(2-hydroxyphenyl)-naphthalene,
2-(2-methoxyphenyl-phenyl)phosphino-1-(2-hydroxyphenyl)-naphthalene,
1-[2-(diphenylphosphino)phenyl]-2-hydroxynaphthalene,
1-[2-(dicyclohexylphosphino)phenyl]-2-hydroxynaphthalene,
1-{2-[bis-(4-fluorophenyl)phosphino|phenyl}-2-hydroxynaphthalene,
1-[2-(4-fluorophenyl-phenyl)phosphino-phenyl]-2-hydroxynaphthalene,
1-[2-(2-methoxyphenyl-phenyl)phosphino-phenyl]-2-hydroxynaphthalene,
2-(diisopropyl)phosphino-1-(2-hydroxyphenyl)naphthalene,
2-[Bis-(4-N,N-dimethylaminophenyl)phosphino]-1-(2-hydroxyphenyl)naphthalene,
2-[bis-(4-N,N-diisopropylaminomethylphenyl)phosphino]-1-(2-hydroxyphenyl)naphthalene,
2-{bis-[3,5-bis-(trifluoromethyl)phenyl]phosphino}-1-(2-hydroxyphenyl)naphthalene,
1-[2-(diisopropylphosphino)phenyl]-2-hydroxynaphthalene,
1-{2-[bis-(4-N,N-dimethylaminophenyl)phosphino]phenyl}-2-hydroxynaphthalene,
1-{2-[bis-(4-N,N-diisopropylaminomethylphenyl)phosphino]-phenyl}-2-hydroxynaphthalene,
1-{2-{bis-[3,5-bis-(trifluoromethyl)phenyl]phosphino}-phenyl}-2-hydroxynaphthalene,
2'-hydroxy-2-[2-methoxyphenyl(phenyl)phosphino]biphenyl,
2'-hydroxy-2-[isopropyl(phenyl)phosphino]biphenyl,
2'-hydroxy-2-[cyclohexyl(phenyl)phosphino|biphenyl,
2-{bis-[3,5-bis-(trifluoromethyl)phenyl]phosphino}-2'-hydroxybiphenyl,
2-diisopropylphosphino-2'-hydroxybiphenyl,
2-[bis-(4-N,N-dimethylaminophenyl)phosphino]-2'-hydroxybiphenyl,
2-[bis-(4-N,N-diisopropylaminomethylphenyl)phosphino]-2'-hydroxybiphenyl,
2-diphenylphosphino-2'-hydroxy-3'-phenylbiphenyl,
2'-hydroxy-2-[2-methoxyphenyl(phenyl)phosphino]-1,1'-biphenyl,
2-{bis-[3,5-bis-(trifluoromethyl)phenyl]phosphino}-2'-hydroxy-1,1'-binaphthyl,
2-diisopropylphosphino-2'-hydroxy-1,1'-binaphthyl,
2-[bis-(4-N,N-dimethylaminophenyl)phosphino]-2'-hydroxy-1,1'-binaphthyl,
2-[bis-(4-N,N-diisopropylaminomethylphenyl)phosphino]-2'-hydroxy-1,1'-binaphthyl,
2'-hydroxy-2-[(isopropylphenyl)phosphino]-1,1'-binaphthyl and
2'-hydroxy-2-[(cyclohexylphenyl)phosphino]-1,1'-binaphthyl.

The following examples describe the invention in more detail without restricting it thereto.
Experimental part

EXAMPLE 1

Preparation of 2'-hydroxy-2-diphenylphosphinobiphenyl 12.3 g (52.4 mmol) of 6-chloro-6H-dibenz[c,e][1,2]oxaphosphorine in 80 ml of anhydrous tetrahydrofuran are introduced, in an argon atmosphere with stirring, and 66 ml of a 2M solution of phenylmagnesium bromide in tetrahydrofuran are added dropwise. The temperature increases in the course of this from 25° to 40° C. The mixture is then stirred for 4 hours at 65° C., cooled to room temperature and 100 ml of water and 100 ml of ethyl acetate are added. The mixture is neutralized with dilute hydrochloric acid, the organic phase is separated off, dried with sodium sulfate and concentrated under reduced pressure. 19.0 g of colorless oil are obtained. By crystallization with methanol/water, 10:1, 18.1 g (98%) of colorless crystals having melting point 123° to 124° C. are obtained.

$^{31}$P-NMR (CDCl$_3$): δ=−11.7 ppm

EXAMPLE 2

2'-Hydroxy-2-[bis-(3-fluorophenyl)phosphino]biphenyl 16.4 g (70 mmol) of 6-chloro-6H-dibenz[c,e][1,2]oxaphosphorine in 80 ml of anhydrous tetrahydrofuran are introduced, in an argon atmosphere with stirring, and a 2M solution of 140 mmol of 3-fluorophenylmagnesium bromide in tetrahydrofuran is added dropwise. The temperature increases in the course of this from 25° to 45° C. The mixture is then stirred for 12 hours at 65° C., cooled to room temperature and 100 ml of water and 100 ml of ethyl acetate are added. The mixture is neutralized with dilute hydrochloric acid, the organic phase is separated off, dried with sodium sulfate and concentrated under reduced pressure. 25.8 g of colorless oil are obtained. By crystallization with methanol/water, 10:1, 19.8 g (71%) of colorless crystals having melting point 161° to 163° C. are obtained.

$^{31}$P-NMR (CDCl$_3$): δ=−11.0 ppm

EXAMPLE 3

Preparation of 2'-hydroxy-2-[bis(1-naphthyl)phosphino]biphenyl 14.1 g (60 mmol) of 6-chloro-6H-dibenz[c,e][1,2]-oxaphosphorine in 50 ml of anhydrous o-xylene are introduced, in an argon atmosphere with stirring, and a solution of 150 mmol of 1-naphthylmagnesium bromide in tetrahydrofuran is added dropwise. The temperature increases in the course of this from 25° to 45° C. The mixture is then stirred for 3 hours at 80° C. and 5 hours at 120° C. The mixture is cooled to room temperature and 100 ml of water are added. The mixture is neutralized with dilute hydrochloric acid, the organic phase is separated off, dried with sodium sulfate and concentrated under reduced pressure. 19.0 g of colorless oil are obtained. By crystallization with methanol/water, 10:1, 22.8 g (89%) of colorless crystals having melting point 255° to 256° C. are obtained.

$^{31}$P-NMR (CDCl$_3$): δ=−30.3 ppm

EXAMPLE 4

Preparation of 2'-hydroxy-2-[(2-methoxyphenylphenyl)phosphino]biphenyl 23.5 g (100 mmol) of 6-chloro-6H-dibenz[c,e][1,2]oxaphosphorine in 50 ml of anhydrous tetrahydrofuran are introduced, in an argon atmosphere with stirring, and a solution of 100 mmol of 2-methoxyphenylmagnesium bromide in tetrahydrofuran is added dropwise at −10° C. The mixture is slowly heated to 25° C. and stirred for 3 hours. A solution of 100 mmol of phenylmagnesium bromide in 150 ml of tetrahydrofuran is added dropwise and the mixture is then stirred for 5 hours at 65° C. The mixture is cooled to room temperature and 100 ml of water are added. The mixture is neutralized with dilute hydrochloric acid, the organic phase is separated off, dried with sodium sulfate and concentrated under reduced pressure. 38.0 g of colorless oil are obtained. By crystallization with methanol/water, 10:1, 32.7 g (86%) of colorless crystals having melting point 137° to 139° C. are obtained.

$^{31}$P-NMR (CDCl$_3$): δ=−22.0 and −23.2 ppm (diastereomer ratio 30:70)

EXAMPLE 5

Preparation of 2'-hydroxy-2-|(2-tolyl-phenyl)phosphino| biphenyl 16.4 g (70 mmol) of 6-chloro-6H-dibenz|c,e||1,2| oxaphosphorine in 50 ml of anhydrous o-xylene are introduced, in an argon atmosphere with stirring, and a solution of 70 mmol of 2-tolylmagnesium bromide in tetrahydrofuran are added dropwise at −10° C. The mixture is slowly heated to 25° C. and stirred for 3 hours. A solution of 70 mmol of phenylmagnesium bromide in 50 ml of diethyl ether is added dropwise and the mixture is then heated to 65° C., the diethyl ether being distilled off. The mixture is stirred for a further 2 hours at 120° C., cooled to room temperature and 100 ml of water are added. The mixture is neutralized with dilute hydrochloric acid, the organic phase is separated off, dried with sodium sulfate and concentrated under reduced pressure. 25.8 g of colorless crystals are obtained. By recrystallization from methanol/water, 10:1, 20.4 g (79%) of colorless crystals having melting point 98 at 101° C. are obtained.

$^{31}$P-NMR (CDCl$_3$): δ=−19.7 and −20.2 ppm (diastereomer ratio 50:50)

EXAMPLE 6

Preparation of 1-(2-hydroxyphenyl)-2-diphenylphosphino-naphthalene 50.8 g (178 mmol) of 6-chloro-6H-benzo[c]naphth[2,1-c]-[1,2]oxaphosphorine in 250 ml of anhydrous o-xylene are introduced, in an argon atmosphere with stirring, and 390 ml of a 2M solution of phenylmagnesium bromide in diethyl ether are added dropwise. The temperature increases in the course of this from 25° to 40° C. The mixture is then slowly heated to 100° C., the diethyl ether distilling off, and is stirred for 3 hours. The mixture is cooled to room temperature and 100 ml of water and 100 ml of ethyl acetate are added. The mixture is neutralized with dilute hydrochloric acid, the organic phase is separated off, dried with sodium sulfate and concentrated under reduced pressure. 70 g of colorless oil are obtained. By crystallization with methanol, 63.8 g (89%) of colorless crystals having melting point 104° to 106° C. are obtained.

$^{31}$P-NMR (CDCl$_3$): δ=−12.0 ppm

EXAMPLE 7

Preparation of 1-(2-diphenylphosphinophenyl)-2-hydroxynaphthalene 9.5 g (33.5 mmol) of 5-chloro-5H-benzo[c]naphth[1,2-e]-[1,2]-oxaphosphorine in 50 ml of anhydrous o-xylene are introduced, in an argon atmosphere with stirring, and 28 ml of a solution of 84 mmol of phenylmagnesium bromide in diethyl ether are added dropwise. The temper-ature increases in the course of this from 25° to 40° C. The mixture is then slowly heated to 100° C., the diethyl ether distilling off, and is stirred for 3 hours. The mixture is cooled to room temperature and 100 ml of water and 100 ml of ethyl acetate are added. The mix-ture is neutralized with dilute hydrochloric acid, the organic phase is separated off, dried with sodium sulfate and concentrated under reduced pressure. 13.5 g of colorless oil are obtained. By crystallization with methanol, 9.5 g (70%) of colorless crystals having melting point 135° to 138° C. are obtained.

$^{31}$P-NMR (CDCl$_3$): δ=−12.7 ppm

EXAMPLE 8

Preparation of 2-|bis-(3-fluorophenyl)phosphino|-1(2-hydroxyphenyl)naphthalene 8.5 g (30 mmol) of 5-chloro-5H-benzo|c|naphth|1,2-e||1,2|-oxa-phosphorine in 50 ml of anhydrous o-xylene at 80° C. are introduced, in an argon atmosphere with stirring, and a solution of 70 mmol of 3-fluorophenylmagnesium bromide in 80 ml of o-xylene is added dropwise. The temperature increases in the course of this from 80° to 90° C. The mixture is then stirred for 1 hour at 110° C. The mixture is cooled to room temperature and 100 ml of water are added. The mixture is neutralized with dilute hydrochloric acid, the organic phase is separated off, dried with sodium sulfate and concentrated under reduced pressure. 19.0 g of colorless oil are obtained.

$^{31}$P-NMR (CDCl$_3$): δ=−3.8 ppm

EXAMPLE 9

Preparation of 2-(dibenzophosphol-9-yl)-2'-hydroxybiphenyl 46 ml of a 1.6M solution of butyllithium in hexane are added dropwise to a solution of 11.4 g (36.54 mmol) of 2,2'-dibromobiphenyl in 60 ml of diethyl ether. The mixture is then stirred for 24 hours at 20° C. To this is then added, at 0C, a solution of 8.6 g (36.5 mmol) of 6-chloro-6H-dibenz [c,e]|1,2]oxaphosphorine in 30 ml of o-xylene. The mixture is then stirred for a further 2 hours at 25° C. and 3 hours at 50° C. The mixture is cooled to room temperature and 100 ml of water are carefully added. The mixture is neutralized with dilute hydrochloric acid, the organic phase is separated off, dried with sodium sulfate and concentrated under reduced pressure. By crystallization of the residue with 2-butanone, 11.8 g (90%) of colorless crystals having melting point 152° to 155° C. are obtained.

$^{31}$P-NMR (CDCl$_3$): δ=−17.8 ppm

EXAMPLE 10

2-{Bis-[3,5-bis-(trifluoromethyl)phenyl]phosphino}-2'-hydroxybiphenyl 23.5 g (0.1 mol) of 6-chloro-6H-dibenz[c,e][1,2] oxaphosphorine in 200 ml of anhydrous o-xylene at 80° C. are introduced, in an argon atmosphere with stirring, and a solution of 0.23 mol of 3,5-di(trifluoromethyl) phenylmagnesium bromide in 300 ml of tetrahydrofuran is added dropwise. Tetrahydrofuran is distilled off and the temperature is slowly increased to 120° C. in the course of this. The mixture is then stirred for 3 hours at 120° C., cooled to room temperature, and 100 ml of water are added. The mixture is neutralized with dilute hydrochloric acid, the organic phase is separated off, dried with sodium sulfate and concentrated under reduced pressure. 61.0 g of black solid are obtained. By recrystallization from heptane, with addition of activated carbon, and subsequent hot filtration, 37.2 g (59%) of pale yellow crystals having melting point 120° to 121° C. are obtained.

$^{31}$P-NMR (CDCl$_3$): δ=−8.4 ppm

EXAMPLE 11

Preparation of 2-diisopropylphosphino-2'-hydroxybiphenyl 46.9 g (0.2 mol) of 6-chloro-6H-dibenz|c,e||1,2]oxaphosphorine in 250 ml of anhydrous o-xylene at 80° C. are introduced, in an argon atmosphere with stirring, and a solution of 0.45 mol of isopropylmagnesium bromide in 300 ml of tetrahydrofuran is added dropwise. Tetrahydrofuran is distilled off and the temperature slowly increased to 120° C. in the course of this. The mixture is then stirred for 3 hours at 120° C., cooled to room temperature and 100 ml of water are added. The mixture is neutralized with concentrated sulfuric acid, heated to 80° C. and the organic phase is separated off. During cooling, 51.7 g (90%) of colorless solid having melting point 82° to 84° C. crystallizes from the aqueous phase. 100 ml of 2N sodium hydroxide solution are added to this solid and the mixture is extracted with toluene. The toluene phase is separated off, washed with water, then dried with sodium sulfate and concentrated in vacuo. 38.9 g (68%) of colorless oil are obtained.

$^{31}$P-NMR (CDCl$_3$): δ=0.3 ppm

EXAMPLE 12

Preparation of 2-[bis-(4-N,N-dimethylaminophenyl) phosphino]-2'-hydroxybiphenyl

A solution of 300 mmol of 4-N,N-dimethylaminophenyl-magnesium bromide in 150 ml of tetrahydrofuran is introduced, in an argon atmosphere with stirring, and 30.5 g (130 mmol) of 6-chloro-6H-dibenz[c,e]-[1,2] oxaphosphorine in 200 ml of anhydrous o-xylene at 80° C. are added dropwise. The temperature increases in the course of this from 80° to 90° C., tetrahydrofuran being distilled off. The mixture is then stirred for 1 hour at 110° C. The mixture is cooled to room temperature and 100 ml of water are added. The mixture is neutralized with dilute hydrochloric acid, the organic phase is separated off, dried with sodium sulfate and concentrated under reduced pressure. After crystallization with methanol, 48.0 g (84%) of colorless crystals having melting point 177° to 178° C. are obtained.

$^{31}$P-NMR (CDCl$_3$): δ=−15.6 ppm

EXAMPLE 13

Preparation of 2-diphenylphosphino-2'-hydroxy-3'-phenyl-biphenyl 23.5 g (0.1 mol) of 6-chloro-6H-4-phenyl-dibenz[c,e][1,2]-oxaphosphorine in 120 ml of anhydrous o-xylene at 80° C. are introduced, in an argon atmosphere with stirring, and a solution of 0.25 mol of phenylmagnesium bromide in 100 ml of diethyl ether is added dropwise. Diethyl ether is distilled off and the temperature slowly increased to 120° C. in the course of this. The mixture is then stirred for 3 hours at 120° C., cooled to room temperature and 100 ml of water are added. The mixture is neutralized with dilute hydrochloric acid, the organic phase is separated off, dried with sodium sulfate and concentrated under reduced pressure. 40.0 g of colorless viscous oil are obtained.

$^{31}$P-NMR (CDCl$_3$): δ=−11.0 ppm

EXAMPLE 14

Preparation of 2-[bis-(4-N,N-diisopropylaminomethyl-phenyl)phosphino]-2'-hydroxybiphenyl A solution of 300 mmol of 4-(N,N-diisopropylaminomethyl)phenylmagnesium bromide in 150 ml of tetrahydrofuran (THF) is introduced, in an argon atmosphere with stirring, and 30.5 g (130 mmol) of 6-chloro-6H-dibenz[c,e][1,2]oxaphosphorine in 200 ml of anhydrous o-xylene are added dropwise at 80° C. The temperature increases from 80° to 90° C., tetrahydrofuran being distilled off in the course of this. The mixture is then stirred for 5 hours at 120° C. The mixture is cooled to room temperature and 100 ml of water are added. The mixture is neutralized with dilute hydrochloric acid, the organic phase is separated off, dried with sodium sulfate and concentrated in vacuo. After crystallization with methanol, 63.3 g (84%) of colorless crystals are obtained.

$^{31}$P-NMR (CDCl$_3$): δ=−12.7 ppm

EXAMPLE 15

Preparation of 2'-{bis-[3,5-bis-(trifluromethyl)phenyl]-phosphino-phenyl}-2-hydroxynaphthalene 6.3 g (22 mmol) of 5-chloro-5H-benzo[c]naphth[1,2-e]-[1,2]oxaphosphorine in 100 ml of anhydrous o-xylene at 80° C. are introduced, in an argon atmosphere with stirring, and a solution of 0.86 mmol of 3,5-bis(trifluoromethyl) phenylmagnesium bromide in 120 ml of tetrahydrofuran is added dropwise to this. Tetrahydrofuran is distilled off and the temperature slowly increased to 120° C. in the course of this. The mixture is then stirred for 4 hours at 120° C., cooled to room temperature and 100 ml of water are added. The mixture is neutralized with dilute hydrochloric acid, the organic phase is separated off, dried with sodium sulfate and concentrated in vacuo. 15.9 g of black solid are obtained. By recrystallization from heptane, with addition of activated carbon, and subsequent hot filtration, 9.5 g (64%) of pale yellow viscous oil are obtained.

$^{31}$P-NMR (CDCl$_3$): δ=−9.7 ppm

EXAMPLE 16

Preparation of 2'-[bis-(di-3,5-fluorophenyl) phosphinophenyl]-2-hydroxynaphthalene 14.0 g (0.049 mol) of 5-chloro-5H-benzo[c]naphth[1,2-e]-[1,2]oxaphosphorine in 100 ml of anhydrous o-xylene at 80° C. are introduced, in an argon atmosphere with stirring, and a solution of 0.15 mol of 3,5-difluorophenylmagnesium bromide in 100 ml of tetrahydrofuran is added dropwise to this. Tetrahydrofuran is distilled off and the temperature slowly increased to 120° C. in the course of this. The mixture is then stirred for 3 hours at 120° C., cooled to room temperature, and 100 ml of water are added. The mixture is neutralized with dilute hydrochloric acid, the organic phase is separated off, dried with sodium sulfate and concentrated in vacuo. 23.3 g of brown oil are obtained. By column chromatography on silica gel using ethyl acetate/n-heptane (2:1) as mobile phase, 13.7 g (59%) of colorless crystals are obtained.

$^{31}$P-NMR (CDCl$_3$): δ=−9.0 ppm

EXAMPLE 17

Preparation of 2-{bis-[3,5-bis-(trifluoromethyl)phenyl]-phosphino}-2'-hydroxy-3'-phenylbiphenyl 10.0 g (0.032 mol) of 6-chloro-6H-4-phenyldibenz[c,e]-([1,2]oxaphosphorine in 100 ml of anhydrous o-xylene at 80° C. are introduced, in an argon atmosphere with stirring, and a solution of 0.086 mol of 3,5-bis(trifluoromethyl)-phenylmagnesium bromide in 100 ml of tetrahydrofuran is added dropwise to this. Tetrahydrofuran is distilled off and the temperature slowly increased to 120° C. in the course of this. The mixture is then stirred for 3 hours at 120° C., cooled to room temperature, and 100 ml of water are added. The mixture is neutralized with dilute hydrochloric acid, the organic phase is separated off, dried with sodium sulfate and concentrated in vacuo. 22.5 g of brown viscous oil are obtained.

$^{31}$P-NMR (CDCl$_3$): δ=−8.0 ppm

EXAMPLE 18

Preparation of 2-[bis-(di-3,5-fluorophenyl)phosphino]-2'-hydroxy-3'-phenylbiphenyl 11.7 g (0.05 mol) of 6-chloro-6H-4-phenyldibenz[c,e][1,2]-oxaphosphorine in 120 ml of anhydrous o-xylene at 80° C. are introduced, in an argon atmosphere with stirring, and a solution of 0.125 mol of 3,5-difluorophenylmagnesium bromide in 100 ml of tetrahydrofuran is added dropwise to this. Tetrahydrofuran is distilled off and the temperature slowly increased to 120° C. in the course of this. The mixture is then stirred for 3 hours at 120° C., cooled to room temperature, and 100 ml of water are added. The mixture is neutralized with dilute hydrochloric acid, the organic phase is separated off, dried with sodium sulfate and concentrated in vacuo. 21.3 g of colorless viscous oil are obtained.

$^{31}$P-NMR (CDCl$_3$): δ=−7.5 ppm

We claim:

1. A hydroxybiarylphosphine of the formula I

     (I)

in which Ar-Ar is biphenyl, 1-phenylnaphthyl or 1,1'-binaphthyl, R$^1$ and R$^2$ are identical or different and are F or alkoxy having in each case 1 to 8 carbon atoms or are substituted aryl, a and b are identical or different and are an integer from 0 to 4, and the Ar-P and the Ar-O bond are each arranged in the ortho-position to the Ar-Ar bond, R$^3$ and R$^4$ are identical or different and are alkyl having 1 to 8 carbon atoms, cycloalkyl having 4 to 10 carbon atoms, alkaryl having 7 to 9 carbon atoms, Ar$^3$-(R$^5$)$_n$, in which Ar$^3$ is an aryl radical having 6 to 10 carbon atoms, R$^5$ is alkoxy having in each case 1 to 8 carbon atoms, CF$_3$, dialkyl-amino having a total of 2 to 8 carbon atoms or —CH$_2$N(alkyl)$_2$ having 1 to 3 carbon atoms per alkyl and n is an integer from 0 to 5, or —R$^3$—R$^4$— forms a chain of 3 to 5 members to which one or two aromatic rings or ring systems having 6 to 10 carbon atoms are optionally fused, and, together with the P atom, forms a ring having 4 to 6 members, with the proviso that Ar$^3$—(R$^5$)$_n$ is not phenyl or a phenyl substituted by halogen, alkyl or alkoxy each having 1 to 8 carbon atoms, if Ar-Ar is biphenyl or 1,1'-binaphthyl and a=b=0 and R$^3$ and R$^4$ are identical in each case.

2. A hydroxybiarylphosphine as claimed in claim 1, wherein R$^1$ and R$^2$ are identical or different and are F or alkoxy having 1 to 4 carbon atoms or are substituted phenyl, a and b are identical or different and are an integer from 0 to 2.

3. A hydroxybiarylphosphine as claimed in claim 1, wherein R$^3$ and R$^4$ are identical or different and are alkyl having 1 to 4 carbon atoms, cycloalkyl having 4 to 6 carbon atoms, benzyl, Ar$^3$—(R$^5$), where Ar$^3$ is an aryl radical having 6 to 10 carbon atoms, R$^5$ is CF$_3$, dialkylamino having a total of 2 to 8 carbon atoms or —CH$_2$N(alkyl)$_2$ having 1 to 3 carbon atoms per alkyl and n is an integer from 0 to 5, with the proviso that Ar$^3$—(R$^5$)$_n$ is not phenyl or a phenyl substituted by halogen, alkyl or alkoxy having in each case 1 to 8 carbon atoms, if Ar-Ar is biphenyl or 1,1'-binaphthyl and a=b=0 and R$^3$ and R$^4$ are identical.

4. A hydroxybiarylphosphine as claimed in claim 1, wherein the radical —PR$^3$R$^4$ is arranged on the phenyl ring of the 1-phenylnaphthyl.

5. A hydroxybiarylphosphine as claimed in claim 1, wherein the radical —PR$^3$R$^4$ is arranged on the naphthyl ring of the 1-phenylnaphthyl.

6. A hydroxybiarylphosphine of the formula I

     (I)

in which the aryl groups Ar-Ar is 1-phenylnaphthyl, R$^1$ and R$^2$ are identical or different and are F, Cl, alkyl or alkoxy having in each case 1 to 8 carbon atoms or are substituted or unsubstituted aryl, a and b are identical or different and are an integer from 0 to 4, and the Ar-P and the Ar-O bond are each arranged in the ortho-position to the Ar-Ar bond, R$^3$ and R$^4$ are identical or different and are alkyl having 1 to 8 carbon atoms, cycloalkyl having 4 to 10 carbon atoms, alkaryl having 7 to 9 carbon atoms, Ar$^3$-(R$^5$)$_n$ in which Ar$^3$ is an aryl radical having 6 to 10 carbon atoms, R$^5$ is alkyl or alkoxy having in each case 1 to 8 carbon atoms, F, Cl, CF$_3$, dialkylamino having a total of 2 to 8 carbon atoms or —CH$_2$N(alkyl)$_2$ having 1 to 3 carbon atoms per alkyl and n is an integer from 0 to 5, or —R$^3$-R$^4$— forms a chain of 3 to 5 members to which one or two aromatic rings or ring systems having 6 to 10 carbon atoms are optionally annulated, and, together with the P atom, forms a ring having 4 to 6 members.

7. A hydroxybiarylphosphine of the formula I

     (I)

in which Ar-Ar is biphenyl, 1-phenylnaphthyl or 1,1'-binaphthyl, R$^1$ and R$^2$ are identical or different and are F or alkoxy having in each case 1 to 8 carbon atoms or are substituted or unsubstituted aryl, a and b are identical or different and are an integer from 0 to 4, and the Ar-P and the Ar-O bond are each arranged in the ortho-position to the Ar-Ar bond, R$^3$ and R$^4$ are identical or different and are alkyl having 1 to 8 carbon atoms, cycloalkyl having 4 to 10 carbon atoms, alkaryl having 7 to 9 carbon atoms, Ar$^3$-(R$^5$)$_n$, in which Ar$^3$ is an aryl radical having 6 to 10 carbon atoms, R$^5$ is CF$_3$, dialkylamino having a total of 2 to 8 carbon atoms or —CH$_2$N(alkyl)$_2$ having 1 to 3 carbon atoms per alkyl and n is an integer from 0 to 5, or —R$^3$-R$^4$— forms a chain of 3 to 5 members to which one or two aromatic rings or ring systems having 6 to 10 carbon atoms are optionally fused, and, together with the P atom, forms a ring having 4 to 6 members, with the proviso that Ar$^3$-(R$^5$)$_n$ is not phenyl or a phenyl substituted by halogen, alkyl or alkoxy each having 1 to 8 carbon atoms, if Ar-Ar is biphenyl or 1,1'-binaphthyl and a=b=0 and R$^3$ and R$^4$ are identical in each case.

8. A hydroxybiarylphosphine as claimed in claim 7, wherein R$^1$ and R$^2$ are identical or different and are F or alkoxy having 1 to 4 carbon atoms or are substituted or unsubstituted phenyl, a and b are identical or different and are an integer from 0 to 2.

9. A hydroxybiarylphosphine as claimed in claim 7, wherein $R^3$ and $R^4$ are identical or different and are alkyl having 1 to 4 carbon atoms, cycloalkyl having 4 to 6 carbon atoms, benzyl, $Ar^3$-$(R^5)$, where $Ar^3$ is an aryl radical having 6 to 10 carbon atoms, $R^5$ is $CF_3$, dialkylamino having a total of 2 to 8 carbon atoms or —$CH_2N(alkyl)_2$ having 1 to 3 carbon atoms per alkyl and n is an integer from 0 to 5, with the proviso that $Ar^3$-$(R^5)_n$ is not phenyl or a phenyl substituted by halogen, alkyl or alkoxy having in each case 1 to 8 carbon atoms, if Ar-Ar is biphenyl or 1,1'-binaphthyl and a=b=0 and $R^3$ and $R^4$ are identical.

10. A hydroxybiarylphosphine as claimed in claim 7, wherein the radical —$PR^3R^4$ is arranged on the phenyl ring of the 1-phenylnaphthyl.

11. A hydroxybiarylphosphine as claimed in claim 7, wherein the radical —$PR^3R^4$ is arranged on the naphthyl ring of the 1-phenylnaphthyl.

* * * * *